United States Patent
Makino (10) Patent No.: US 9,439,559 B2
(45) Date of Patent: Sep. 13, 2016

(54) IMAGE PICKUP APPARATUS AND ELECTRONIC DEVICE USING THE SAME

(71) Applicant: OLYMPUS CORPORATION, Tokyo (JP)

(72) Inventor: Yukiharu Makino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 284 days.

(21) Appl. No.: 14/105,311

(22) Filed: Dec. 13, 2013

(65) Prior Publication Data

US 2014/0098208 A1   Apr. 10, 2014

Related U.S. Application Data

(63) Continuation of application No. PCT/JP2012/064463, filed on Jun. 5, 2012.

(30) Foreign Application Priority Data

Jun. 13, 2011 (JP) ................................. 2011-131472

(51) Int. Cl.
  *A61B 1/04* (2006.01)
  *H04N 5/225* (2006.01)

(52) U.S. Cl.
  CPC .............. *A61B 1/041* (2013.01); *H04N 5/2253* (2013.01); *H04N 2005/2255* (2013.01)

(58) Field of Classification Search
  CPC ........... A61B 1/041; H04N 2005/225; H04N 5/2253
  USPC ........................................................... 348/76
  See application file for complete search history.

(56) References Cited

U.S. PATENT DOCUMENTS

| 5,021,888 A | 6/1991 | Kondou et al. |
| 6,002,437 A * | 12/1999 | Morioka et al. ............... 348/373 |
| 2003/0034394 A1 * | 2/2003 | Gannon et al. ............... 235/454 |

(Continued)

FOREIGN PATENT DOCUMENTS

| EP | 1 148 716 A1 | 10/2001 |
| JP | 2004-173028 A | 6/2004 |

(Continued)

OTHER PUBLICATIONS

Extended Supplementary European Search Report dated Jan. 8, 2015 from related European Application No. 13 80 1353.9.

(Continued)

*Primary Examiner* — Shan Elahi
(74) *Attorney, Agent, or Firm* — Scully, Scott, Murphy & Presser, PC (57) ABSTRACT

An image pickup device constituted by a bare chip is mounted to a flexible substrate including an opening portion and a wiring pattern, so that a light receiving area is positioned at the opening portion and so as to be electrically connected to the wiring pattern. A rigid substrate having a concave portion capable of housing the image pickup device is connected to the flexible substrate. A bottom face of the concave portion is set as a reference face for regulating the optical axis direction of the image pickup device, and a rear face of the image pickup device is firmly fixed to the bottom face. A wiring pattern is provided on the rigid substrate, and the wiring pattern of the rigid substrate and the wiring pattern of the flexible substrate are electrically connected.

6 Claims, 8 Drawing Sheets

| 10 - | image pickup apparatus | 26 - | electronic components |
| 11 - | image pickup device | 30 - | rigid substrate |
| 11a - | light receiving area | 31 - | concave portion |
| 13 - | electrically conductive bumps | 31a - | bottom face |
| 20 - | flexible substrate | 32 - | wiring pattern |
| 21 - | opening portion | 33 - | terminal portions |
| 22 - | wiring pattern | 34 - | electronic components |
| 23 - | terminal portions | 35 - | non-conductive adhesive |
| 24 - | electrodes | O - | optical axis |
| 25 - | non-conductive adhesive | t1 - | thickness of the image pickup device |
| | | d1 - | depth of the concave portion |

(56) References Cited

U.S. PATENT DOCUMENTS

| | | | |
|---|---|---|---|
| 2003/0223008 A1* | 12/2003 | Kim et al. | 348/340 |
| 2004/0130640 A1 | 7/2004 | Fujimori | |
| 2005/0279916 A1* | 12/2005 | Kang et al. | 250/208.1 |
| 2007/0002546 A1* | 1/2007 | Nomura et al. | 361/748 |
| 2008/0246868 A1* | 10/2008 | Abe | 348/308 |
| 2008/0304821 A1* | 12/2008 | Jeung et al. | 396/529 |
| 2009/0166511 A1* | 7/2009 | Kwon et al. | 250/206 |
| 2009/0201399 A1 | 8/2009 | Senga | |
| 2009/0212397 A1* | 8/2009 | Tuttle | H01L 27/14634 257/618 |
| 2009/0256931 A1* | 10/2009 | Lee et al. | 348/231.99 |
| 2010/0103296 A1 | 4/2010 | Nakagiri et al. | |
| 2010/0265349 A1* | 10/2010 | Kim et al. | 348/222.1 |
| 2011/0074963 A1* | 3/2011 | Awazu | G03B 5/00 348/208.4 |
| 2011/0084118 A1 | 4/2011 | Wada et al. | |
| 2011/0255250 A1* | 10/2011 | Dinh | G03B 15/03 361/749 |
| 2011/0255850 A1* | 10/2011 | Dinh | G03B 15/03 396/176 |
| 2011/0285890 A1* | 11/2011 | Choi et al. | 348/308 |
| 2013/0220680 A1* | 8/2013 | Tazawa | H01L 21/4867 174/255 |

FOREIGN PATENT DOCUMENTS

| | | |
|---|---|---|
| JP | 2008-312104 A | 12/2008 |
| JP | 2009-186796 A | 8/2009 |
| JP | 2009-188828 A | 8/2009 |
| JP | 2010-283443 A | 12/2010 |
| JP | 2011-086670 A | 4/2011 |

OTHER PUBLICATIONS

International Search Report dated Jul. 3, 2012 issued in PCT/JP2012/064463.

European Patent Communication dated Sep. 30, 2015, from corresponding European Application No. 12 801 353.9.

* cited by examiner

- 10 - image pickup apparatus
- 11 - image pickup device
- 11a - light receiving area
- 20 - flexible substrate
- 21 - opening portion
- 26 - electronic components
- 30 - rigid substrate
- 35 - non-conductive adhesive

- 10 - image pickup apparatus
- 11 - image pickup device
- 11a - light receiving area
- 13 - electrically conductive bumps
- 20 - flexible substrate
- 21 - opening portion
- 22 - wiring pattern
- 23 - terminal portions
- 24 - electrodes
- 25 - non-conductive adhesive
- 26 - electronic components
- 30 - rigid substrate
- 31 - concave portion
- 31a - bottom face
- 32 - wiring pattern
- 33 - terminal portions
- 34 - electronic components
- 35 - non-conductive adhesive
- O - optical axis
- t1 - thickness of the image pickup device
- d1 - depth of the concave portion

IMAGE PICKUP APPARATUS AND ELECTRONIC DEVICE USING THE SAME

CROSS REFERENCE TO RELATED APPLICATION

This application is a continuation application of PCT/JP2012/064463 filed on Jun. 5, 2012 and claims benefit of Japanese Application No. 2011-131472 filed in Japan on Jun. 13, 2011, the entire contents of which are incorporated herein by this reference.

BACKGROUND OF THE INVENTION

1. Field of the Invention

The present invention relates to an image pickup apparatus in which an image pickup device constituted by a bare chip is mounted on a flexible substrate, and an electronic device that uses the image pickup apparatus.

2. Description of the Related Art

An image pickup apparatus in which an image pickup device constituted by a bare chip is mounted on a flexible substrate is already known as an image pickup apparatus that is favorably used in a comparatively small electronic device such as an electronic endoscope, a capsule endoscope or a digital camera.

As this kind of image pickup apparatus, for example, Japanese Patent Application Laid-Open Publication No. 2004-173028 discloses technology in which a solid-state image pickup apparatus is constructed by: electrically connecting a solid-state image pickup device (image pickup device) constituted by a bare chip by means of an adhesive through a projecting electrode to a wiring pattern formed on one surface of a substrate having an opening portion that is opposed to a light receiving area of the image pickup device; attaching a translucent member to the other surface of the substrate so as to seal the opening portion; and attaching a sealing member having a concave portion that is capable of housing the solid-state image pickup device to the substrate from a rear face side of the solid-state image pickup device so as to surround and hermetically seal the solid-state image pickup device.

By adopting this configuration, the height of the image pickup apparatus disclosed in Japanese Patent Application Laid-Open Publication No. 2004-173028 can be lowered in comparison to an image pickup apparatus that employs a wire bonding method in which a terminal of a bare chip is intermetallically connected via a gold wire or the like to a ceramic substrate or the like. Furthermore, if various electronic components or the like belonging to the solid-state image pickup device are mounted on the flexible substrate, there is no necessity to separately add a dedicated substrate for mounting the various electronic components or the like, and consequently it is possible to further lower the height of the image pickup apparatus and reduce the size thereof. In addition, according to the technology disclosed in the aforementioned Japanese Patent Application Laid-Open Publication No. 2004-173028, by adopting a flexible substrate as the substrate on which to mount the solid-state image pickup device, it is possible to secure a suitable degree of layout freedom when incorporating the image pickup apparatus into various electronic devices.

SUMMARY OF THE INVENTION

An image pickup apparatus according to one aspect of the present invention includes: a flexible substrate having an opening portion and a wiring pattern; an image pickup device constituted by a bare chip that is mounted to the flexible substrate so that a light receiving area is positioned at the opening portion, and so as to be electrically connected to the wiring pattern; and a rigid substrate having a concave portion capable of housing the image pickup device, and a wiring pattern; wherein at least one section of the concave portion of the rigid substrate is set as a reference face for regulating an optical axis direction of the image pickup device, and at least one section of a rear face of the light receiving area in the image pickup device is firmly fixed to the reference face; and the wiring pattern of the flexible substrate and the wiring pattern of the rigid substrate are electrically connected.

Further, an electronic device according to an aspect of the present invention is an electronic device in which the image pickup apparatus is mounted.

DETAILED DESCRIPTION OF THE PREFERRED EMBODIMENTS

Figure 1:
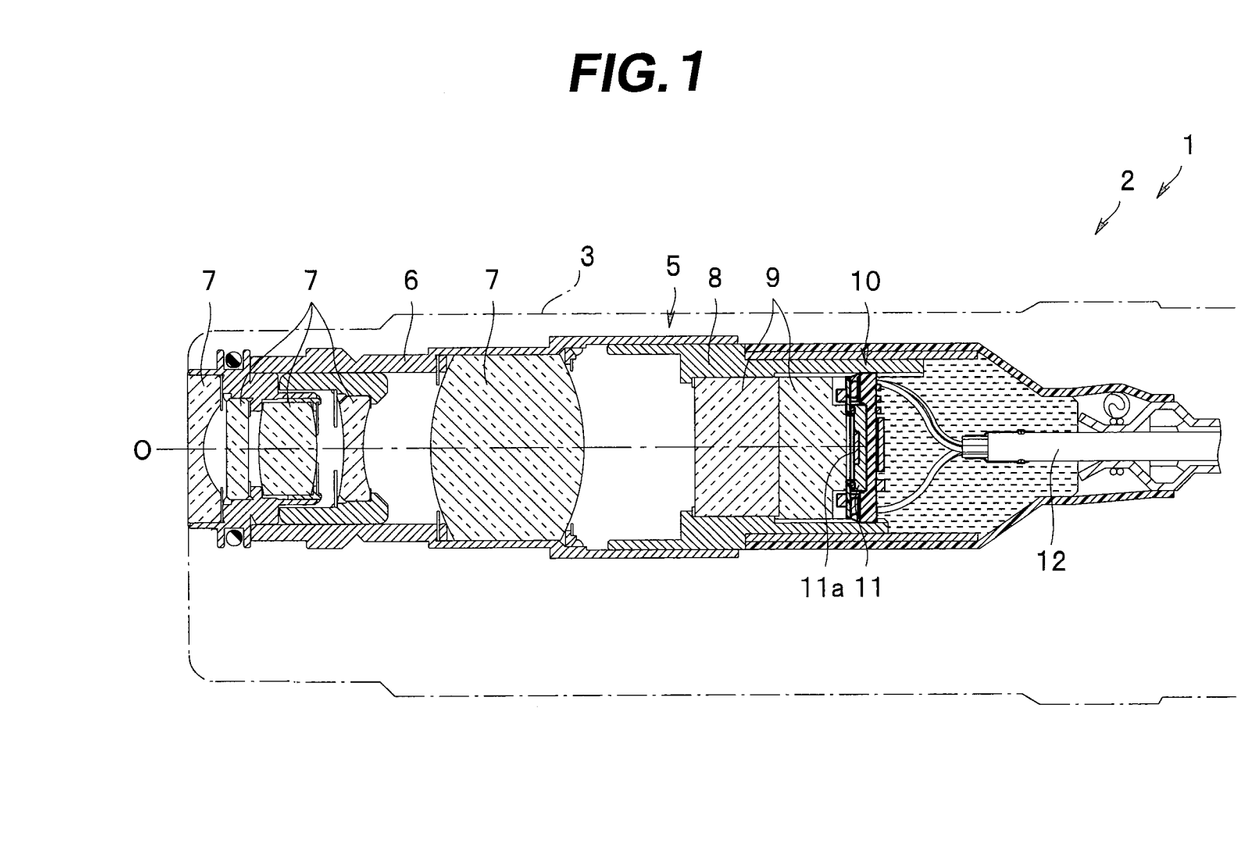
FIG. 1 is a sectional view of main parts of an endoscope distal end portion in which an image pickup apparatus is mounted according to a first embodiment of the present invention.
Figure 2:
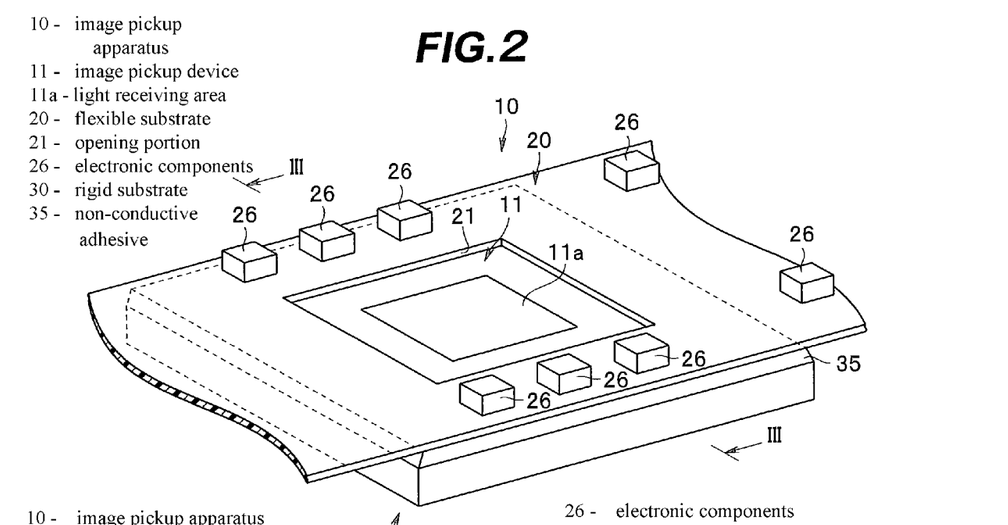
FIG. 2 is a perspective view of the image pickup apparatus according to the first embodiment of the present invention.
Figure 3:
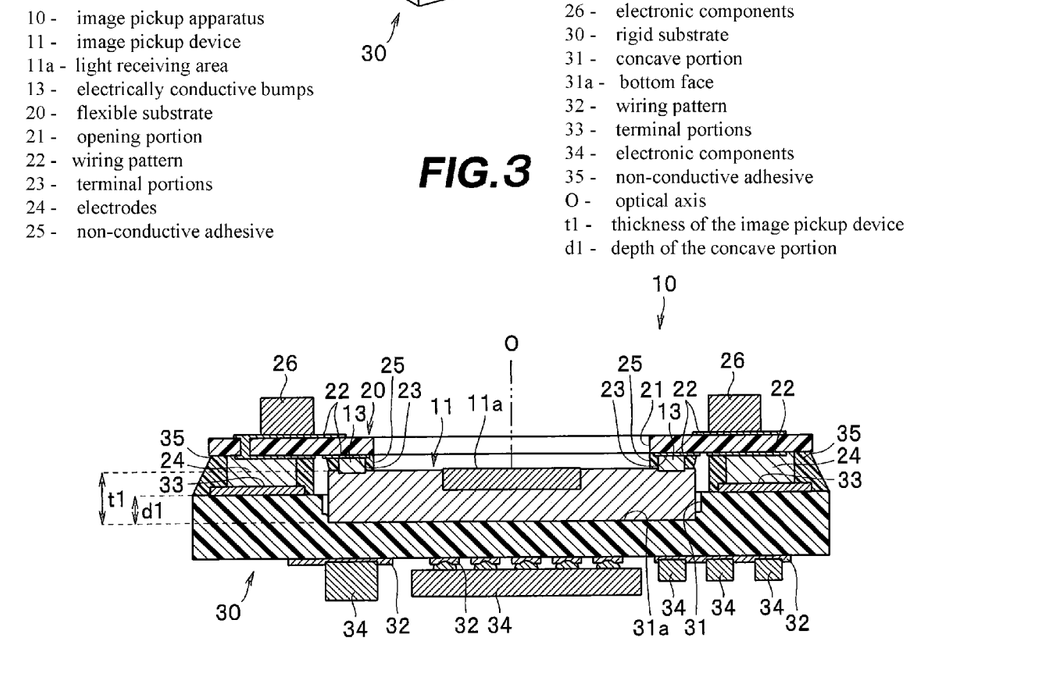
FIG. 3 is a sectional view along a line III-III in FIG. 2 of the image pickup apparatus according to the first embodiment of the present invention.
Figure 4:
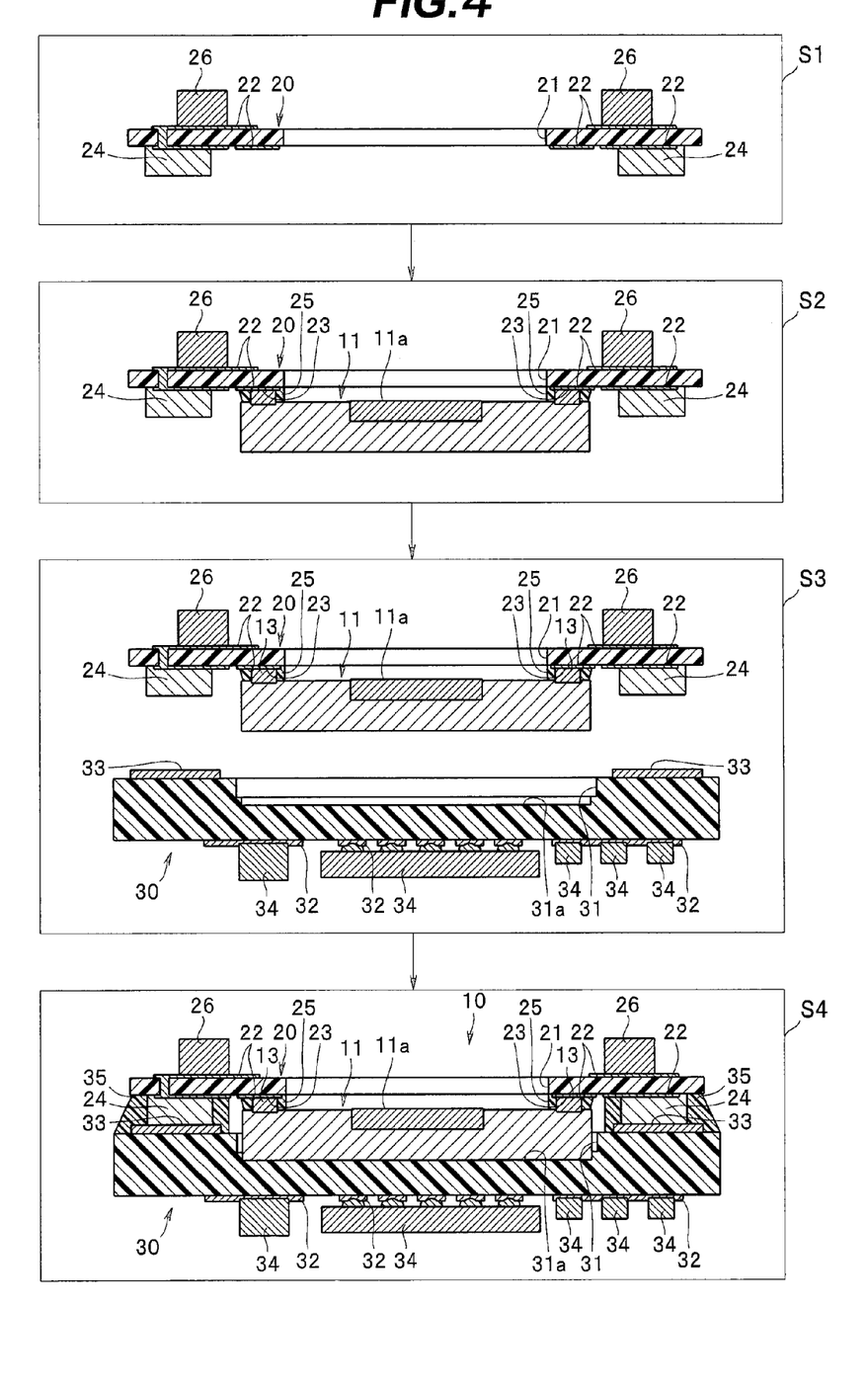
FIG. 4 is an explanatory view illustrating a process for manufacturing the image pickup apparatus according to the first embodiment of the present invention.

Embodiments of the present invention are described hereunder with reference to the drawings. FIG. 1 to FIG. 4 relate to a first embodiment of the present invention. FIG. 1 is a sectional view of main parts of an endoscope distal end portion in which an image pickup apparatus is mounted. FIG. 2 is a perspective view of the image pickup apparatus. FIG. 3 is a sectional view along a line III-III in FIG. 2. FIG. 4 is an explanatory view illustrating a process for manufacturing the image pickup apparatus. Note that the components in the respective drawings used in the following description are each displayed in a different contraction scale so as to be shown in a size that is recognizable in the drawings. Further, the present invention is not limited to only the quantity of components, the shapes of components, the ratios between the sizes of components, and the relative positional relationship between the respective components illustrated in the drawings.

In FIG. 1, an endoscope 1 that is shown as one example of an electronic device includes an image pickup unit 5 inside a distal end rigid portion 3 that is provided at a distal end of a long insertion portion 2. The image pickup unit 5 has a lens barrel 6 that holds a plurality of lenses 7, and an image sensor barrel 8 that is connected to a proximal portion side of the lens barrel 6. A pair of cover glasses 9 and an image pickup apparatus 10, for example, are held inside the image sensor barrel 8. A light receiving area 11a that is set in an image pickup device 11 of the image pickup apparatus 10 is arranged on an optical axis O of the respective lenses 7 in the lens barrel 6. A cable 12 for transmitting signals is electrically connected to the image pickup apparatus 10.

As shown in FIGS. 2 and 3, the image pickup apparatus 10, for example, includes the image pickup device 11, a flexible substrate 20 on which the image pickup device 11 is mounted, and a rigid substrate 30 that is electrically connected to the flexible substrate 20.

The image pickup device 11, for example, is constituted by a semiconductor bare-chip substrate such as a CCD (charge coupled device) or a CMOS (complementary metal oxide semiconductor image sensor). A light receiving area 11a is formed on one surface (front face) side of the image pickup device 11. Further, on the front face side of the image pickup device 11, a plurality of electrically conductive bumps 13 formed of, for example, gold bumps are formed in an edge region that surrounds the light receiving area 11a.

An opening portion 21 that penetrates the flexible substrate 20 in the thickness direction is formed therein in correspondence with the light receiving area 11a of the image pickup device 11. A predetermined wiring pattern 22 is formed on the flexible substrate 20. In addition, a plurality of terminal portions 23 corresponding to each of the electrically conductive bumps 13 of the image pickup device 11 are formed on the wiring pattern 22 that is exposed on the other surface (rear face) side of the flexible substrate 20. Electrodes 24 for electrically connecting with the rigid substrate 30 are also provided in a protruding condition on the wiring pattern 22 that is exposed on the rear face side of the flexible substrate 20.

The image pickup device 11 is mounted in a predetermined positioned state with respect to the flexible substrate 20 that is constructed as described above. More specifically, the image pickup device 11 is connected to the rear face side of the flexible substrate 20 in a mechanically positioned state so that the light receiving area 11a faces the opening portion 21, and the respective electrically conductive bumps 13 electrically connect with the respective terminal portions 23.

Further, various electronic components 26 including chip components such as a resistance or an LED are mounted at appropriate positions on the flexible substrate 20, and these components are electrically connected to the wiring pattern 22.

A bottomed concave portion 31 for housing the image pickup device 11 is formed on one surface (front face) side of the rigid substrate 30. In the present embodiment, a bottom face 31a of the concave portion 31 is formed as a flat face that is capable of contacting against the rear face of the image pickup device 11, and a depth d1 thereof (that is, a depth from the front face of the rigid substrate 30 to the bottom face 31a) is set so as to be equal to or less than a thickness t1 of the image pickup device 11.

A predetermined wiring pattern 32 is formed on the rigid substrate 30. On the front face side of the rigid substrate 30, terminal portions 33 that correspond to the electrodes 24 of the flexible substrate 20 are formed on the wiring pattern 32.

The rigid substrate 30 constructed as described above is joined in a predetermined positioned state to the rear face side of the flexible substrate 20 and thereto. More specifically, the rigid substrate 30 is connected to the rear face side of the flexible substrate 20 in a mechanically positioned state so that the image pickup device 11 is housed in the concave portion 31 and the respective terminal portions 33 are electrically connected to the respective electrodes 24.

When joining the rigid substrate 30 to the flexible substrate 20, for example, the rear face side of the image pickup device 11 is fitted into the concave portion 31 and firmly fixed thereto, and is held in a state in which the rear face is pushed against the bottom face 31a. As a result, the optical axis direction of the image pickup device 11 that is mounted in the flexible substrate 20 is unambiguously regulated in a manner that follows the bottom face. That is, the bottom face 31a of the concave portion 31 functions as a reference face for regulating the optical axis direction of the image pickup device 11 as a result of the rear face side of the image pickup device 11 being firmly fixed to the bottom face 31a in substantially a state of tight contact therebetween.

Further, various electronic components 34 including chip components such as a resistance or an LED are mounted at appropriate positions on the rigid substrate 30, and these components are electrically connected to the wiring pattern 32.

In this case, a non-conductive adhesive 25 is used for the mechanical connection between the flexible substrate 20 and the image pickup device 11. By providing the non-conductive adhesive 25 around the periphery of the light receiving area 11a so as to surround the light receiving area 11a, an annular region of an edge portion on the front face side of the image pickup device 11 is joined in a watertight manner to the flexible substrate 20. Similarly, a non-conductive adhesive 35 is used for the mechanical connection between the flexible substrate 20 and the rigid substrate 30, and by providing the non-conductive adhesive 35 around the periphery of the concave portion 31 so as to surround the periphery thereof, an annular region of an edge portion on the front face side of the rigid substrate 30 is joined in a watertight manner to the flexible substrate 20. The rear face side of the image pickup device 11 is sealed in a watertight manner inside the concave portion 31 by means of the joints formed through the non-conductive adhesives 25 and 35.

Next, an example of a method of manufacturing the image pickup apparatus 10 configured as described above is described in accordance with a procedure illustrated in FIG. 4.

According to this method of manufacturing the image pickup apparatus 10, first, in a process in step S1, the various electronic components 26 are mounted on the flexible substrate 20.

Next, in a process in step S2, the image pickup device 11 is introduced, and after the image pickup device 11 is mechanically positioned with respect to the rear face side of the flexible substrate 20, the image pickup device 11 is mounted thereto through the non-conductive adhesive 25.

Subsequently, in a process in step S3, the rigid substrate 30 is introduced, and the various electronic components 34 are mounted on the rigid substrate 30.

Next, in a process in step S4, after the rigid substrate 30 is mechanically positioned with respect to the rear face side of the flexible substrate 20, the rigid substrate 30 is joined thereto through the non-conductive adhesive 35. At this time, because the rear face side of the image pickup device 11 on which the flexible substrate 20 is mounted is fitted into the concave portion 31 of the rigid substrate 30 and firmly fixed thereto, and the rear face of the image pickup device 11 is brought into contact against the bottom face 31a of the concave portion 31, the optical axis direction of the image pickup device 11 on the image pickup apparatus 10 is unambiguously regulated.

According to this embodiment, a reduction in the height of the image pickup apparatus 10 can be favorably realized by mounting the image pickup device 11 constituted by a bare chip to the flexible substrate 20 having the opening portion 21 and the wiring pattern 22 so that the light receiving area 11a is positioned at the opening portion 21 and the electrically conductive bumps 13 are electrically connected to the terminal portions 23 (wiring pattern 22). In addition, by connecting the rigid substrate 30 having the concave portion 31 capable of housing the image pickup device 11 to the flexible substrate 20 and also setting the bottom face 31a of the concave portion 31 as a reference face and fixing the rear face of the image pickup device 11 to the bottom face 31a to thereby regulate the optical axis direction of the image pickup device 11, it is possible to accurately suppress variations in the image pickup direction of the image pickup apparatus 10 also in a case where the flexible substrate 20 is used as a mounting substrate of the image pickup device 11. In this case, in particular, by forming the concave portion 31 in the rigid substrate 30 and housing the image pickup device 11 in the concave portion 31, the concave portion 31 can be made to also function as an enclosing member for enclosing the rear face side of the image pickup device 11 while retaining the reduction in height of the image pickup apparatus 10. In addition, by providing the wiring pattern 32 on the rigid substrate 30 and electrically connecting the wiring pattern 32 of the rigid substrate 30 and the wiring pattern 22 of the flexible substrate 20, the rigid substrate 30 can be made to also serve a function as a substrate for mounting the various electronic components 34 belonging to the image pickup device 11, and thus a more favorable reduction in the height of the image pickup apparatus 10 can be realized.

In this case, by setting the depth d1 of the concave portion 31 of the rigid substrate 30 so as to be equal to or less than the thickness t1 of the image pickup device 11, a situation in which the rear face of the image pickup device 11 separates from the bottom face 31a of the concave portion 31 due to the elasticity of the flexible substrate 20 or the like can be reliably prevented.

Further, by mounting the image pickup apparatus 10 in an electronic device such as the endoscope 1, the image pickup direction can be accurately set and a reduction in the size of the electronic device can be favorably realized.

Figure 5:
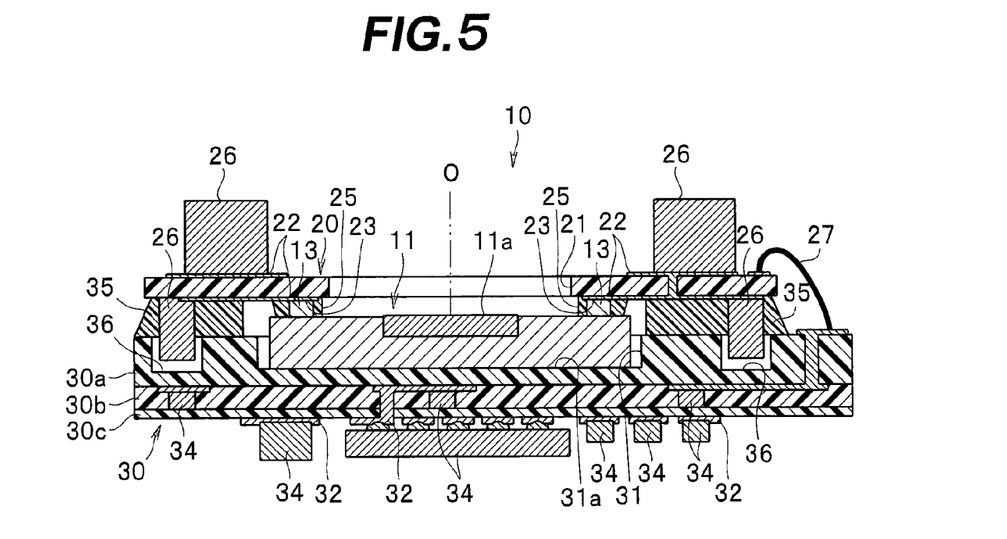
FIG. 5 is a sectional view of main parts of an image pickup apparatus according to a second embodiment of the present invention.

Next, FIG. 5 is a sectional view of main parts of an image pickup apparatus that relates to a second embodiment of the present invention. Note that, in the present embodiment, components that are the same as in the foregoing first embodiment are denoted by the same reference characters and a description of such components is omitted.

As shown in FIG. 5, in the image pickup apparatus 10 according to the present embodiment, the electronic components 26 are mounted not only on the front face side but also on the rear face side of the flexible substrate 20. In this case, it is preferable to form concave portions 36 in the rigid substrate 30 at positions corresponding to the electronic components 26 mounted on the rear face side of the flexible substrate 20, and it is preferable to set the depth of the concave portions 36 so as to be deeper than the height of the electronic components 26. Further, the rigid substrate 30 of the present embodiment is constituted by a substrate having a multi-layered structure (for example, a three-layer structure), and electronic components 34 are arbitrarily mounted in respective layers 30a, 30b, and 30c of the rigid substrate 30.

Note that in the present embodiment an electrical connection between the flexible substrate 20 and the rigid substrate 30 is made by means of wire bonding using a gold wire 27, for example.

According to this embodiment, in addition to the advantages obtained by the above described first embodiment, high-density mounting of electronic components can be performed more efficiently and a further reduction in the height of the image pickup apparatus can be achieved.

Figure 6:
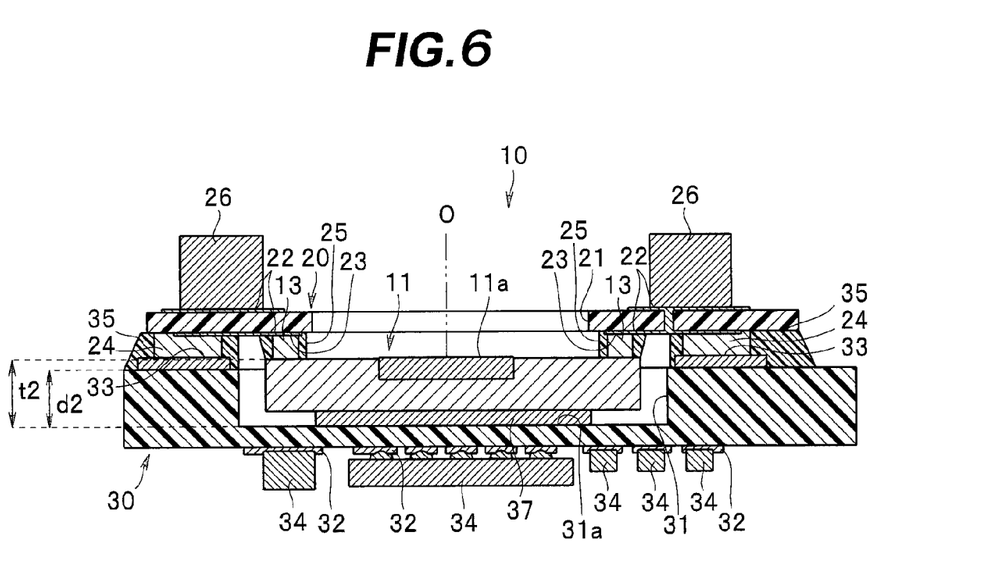
FIG. 6 is a sectional view of main parts of an image pickup apparatus according to a third embodiment of the present invention.

Next, FIG. 6 is a sectional view of main parts of an image pickup apparatus that relates to a third embodiment of the present invention. Note that, in the present embodiment, components that are the same as in the foregoing first embodiment are denoted by the same reference characters and a description of such components is omitted.

As shown in FIG. 6, in the image pickup apparatus 10 of the present embodiment, the rear face of the image pickup device 11 is firmly fixed to the bottom face 31a of the concave portion 31 via an intervening spacer 37.

In this case it is preferable that the spacer 37 of the present embodiment be constituted by, for example, a metal member having high thermal conductivity. Further, a depth d2 of the concave portion 31 that is formed in the rigid substrate 30 is preferably set so as to be less than or equal to a sum t2 of the thickness of the image pickup device 11 and the thickness of the spacer 37.

According to this embodiment, in addition to the advantages obtained by the above described first embodiment, it is possible for heat generated at the image pickup device 11 to be quickly dissipated via the spacer 37.

Figure 7:
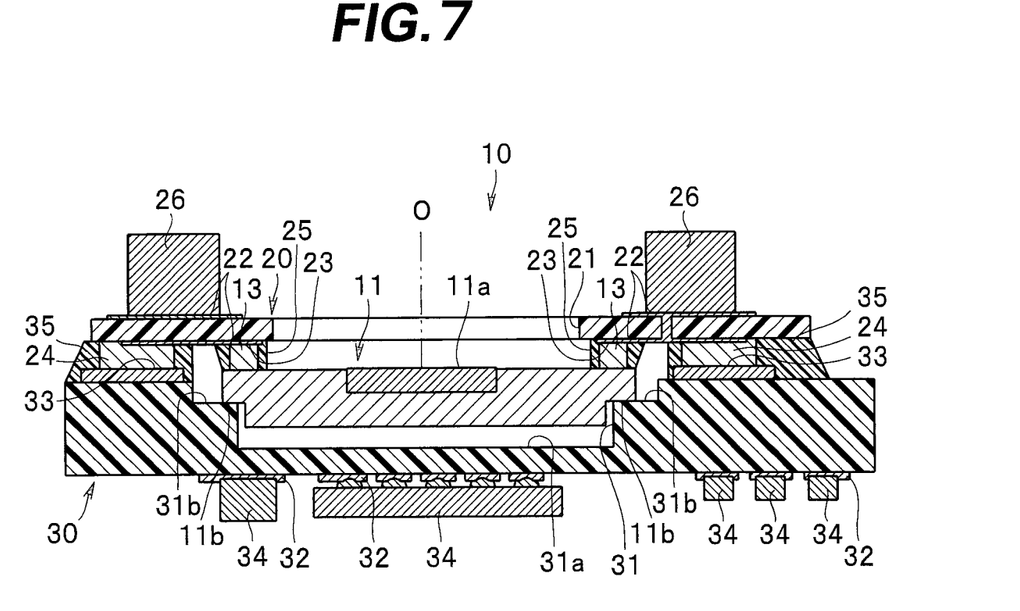
FIG. 7 is a sectional view of main parts of an image pickup apparatus relating to a fourth embodiment of the present invention.

FIG. 7 is a sectional view of main parts of an image pickup apparatus that relates to a fourth embodiment of the present invention. Note that, in the present embodiment, components that are the same as in the foregoing first embodiment are denoted by the same reference characters and a description of such components is omitted.

As shown in FIG. 7, according to the image pickup apparatus 10 of the present embodiment, in the concave portion 31 of the rigid substrate 30, a step portion 31b is formed at a position that is shallower than the bottom face 31a. The step portion 31b is set as a reference face that regulates the optical axis direction of the image pickup device 11.

On the other hand, on the rear face side of the image pickup device 11, a step portion 11b is formed that corresponds to the step portion 31b formed in the concave portion 31, and the step portion 11b is set as a fixation face.

The optical axis O direction of the image pickup device 11 is regulated by fixation between the step portions 11b and 31b that are set in the image pickup device 11 and the concave portion 31.

According to this embodiment, in addition to the advantages obtained by the above described first embodiment, by causing the step portion 11b that is set in the image pickup device 11 to contact against the step portion 31b of the concave portion 31, it is possible to regulate the optical axis O direction of the image pickup device 11 with higher precision.

In this connection, in the respective embodiments described above, although examples are described in which the image pickup apparatus 10 is mounted in the endoscope 1, an electronic device to which the image pickup apparatus 10 can be applied is not limited to the endoscope 1, and naturally the image pickup apparatus 10 can also be mounted in other electronic devices.

Figure 8:
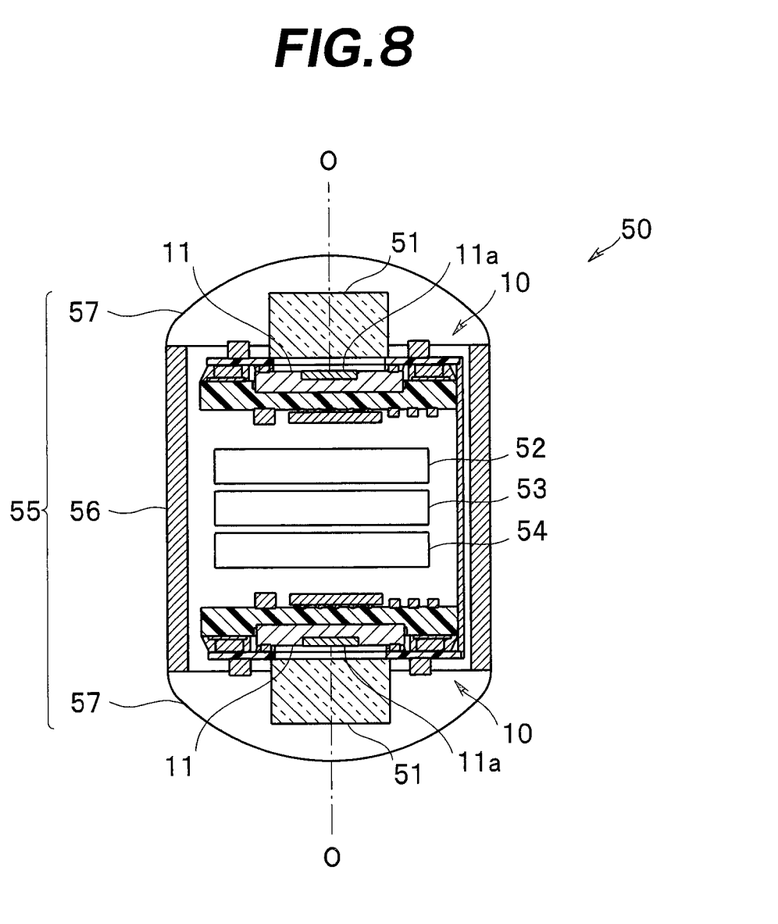
FIG. 8 is a schematic configuration diagram of a capsule endoscope in which an image pickup apparatus is mounted.

For example, as shown in FIG. 8, it is also possible to mount the image pickup apparatus 10 in a capsule endoscope 50. The capsule endoscope 50 exemplified in FIG. 8 includes as main parts: a pair of image pickup apparatuses 10, an optical member (lens unit) 51, a signal processing circuit unit 52 that processes image pickup signals from the image pickup apparatuses 10, a battery 53 as a power source unit, and an RF unit 54 that performs radio transmission of an image signal that underwent signal processing at the signal processing circuit unit 52 to an external device. The aforementioned components are housed inside an exterior case 55 that is an airtight container. The exterior case 55, for example, includes an outer barrel member 56 that has a substantially cylindrical shape, and a pair of cover members 57 that are substantially hemispherical dome members. The interior of the exterior case 55 is sealed in a watertight condition by the respective cover members 57 being fitted and bonded so as to block the opening portions at both ends of the outer barrel member 56. Note that the respective cover members 57 of the exterior case 55 are constituted by an optical dome having optical transparency, and the light receiving area 11a of each image pickup apparatus 10 is disposed so as to face the corresponding cover member 57 via the optical member 51.

Figure 9:
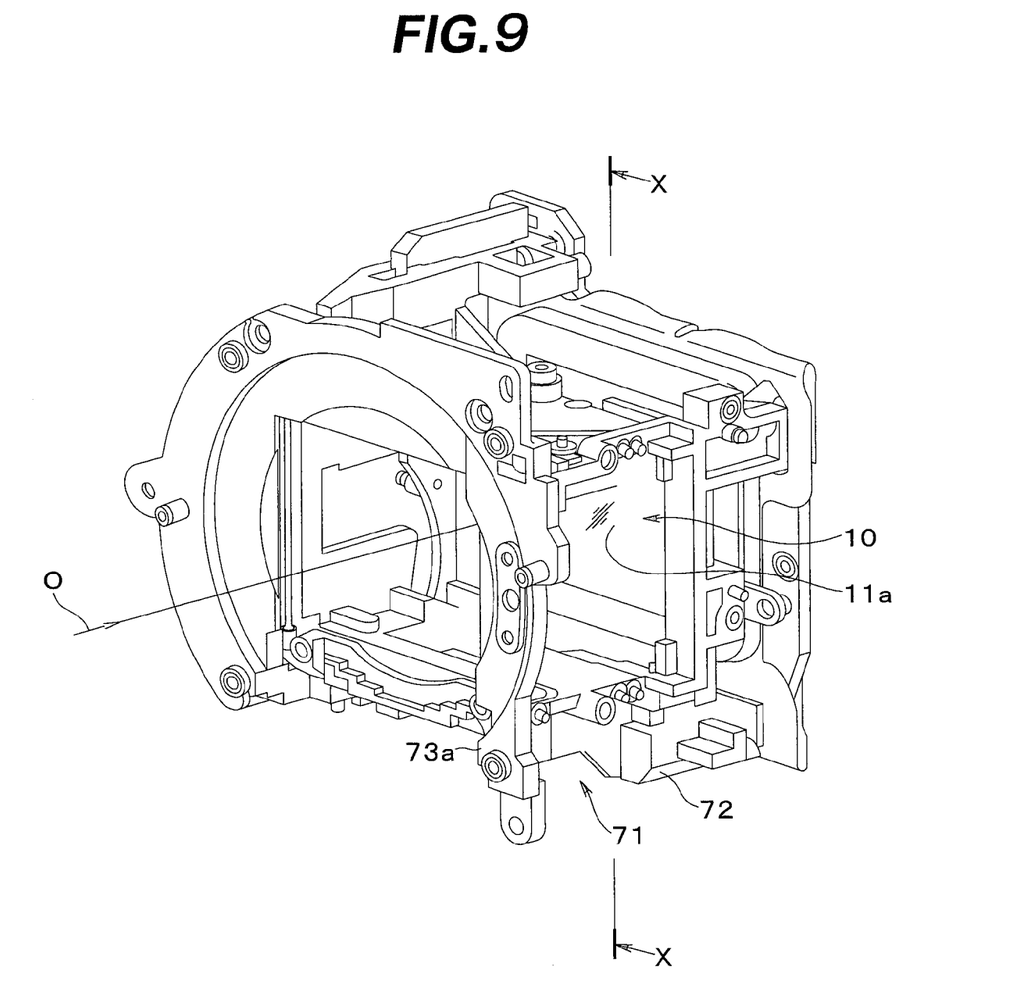
FIG. 9 is a perspective view illustrating main parts of a digital camera in which an image pickup apparatus is mounted.
Figure 10:
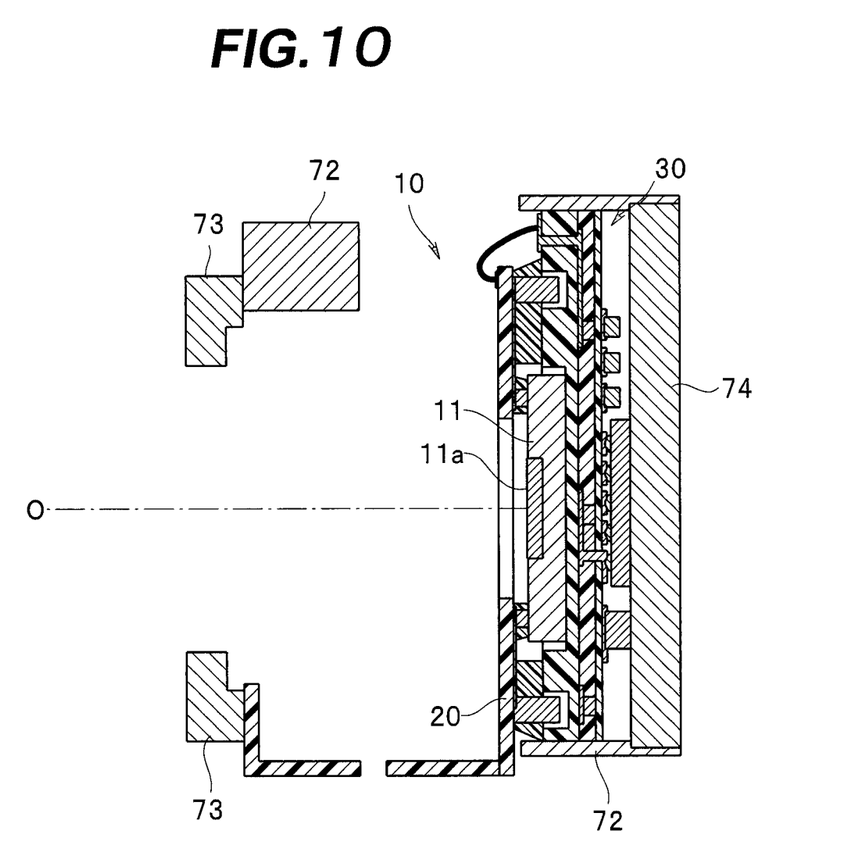
FIG. 10 is a sectional view schematically illustrating main parts along a line X-X in FIG. 9.

Furthermore, for example, as shown in FIGS. 9 and 10, it is also possible to mount the image pickup apparatus 10 in a digital camera. The main parts of the digital camera exemplified in FIGS. 9 and 10 relate to a digital single-lens reflex camera. A mount mounting surface 73a onto which a body mount 73 is mounted is set at a front face of a main body portion 72 of a mirror box 71 that is a main part of the digital camera. The body mount 73 is provided so that a taking lens barrel (not shown) that has a photographing optical system can be detachably attached to the main body portion 72. Accordingly, the body mount 73 is set so that when the taking lens barrel is mounted thereto, the optical axis O of the photographing optical system of the taking lens barrel passes through substantially the center of the body mount 73 and, furthermore, so that the mount surface of the body mount 73 is substantially perpendicular to the optical axis O of the photographing optical system. At the rear of the main body portion 72, a plate-like fixing member 74 is arranged that is disposed parallel to the body mount 73, and the rear face side of the image pickup apparatus 10 is fixedly installed in the main body portion 72 via the fixing member 74.

Note that although in each of the above described embodiments an example was described in which gold bumps are used as electrically conductive bumps, the present invention is not limited thereto, and for example solder bumps (solder balls) or the like may also be used.

Further, although in each of the above described embodiments an example was described in which a non-conductive adhesive is used to bond the image pickup device and the flexible substrate together, or to bond the flexible substrate and the rigid substrate together, the present invention is not limited thereto. For example, an NCF (non-conductive film), an ACP (anisotropic conductive paste), an ACF (anisotropic conductive film), a photosensitive adhesive, or a photosensitive adhesive film may also be used.

Electronic components to be mounted on the flexible substrate or the rigid substrate are also not limited to the components described in each of the above described embodiments, and various electronic components such as, for example, a signal processing driver IC, a diode, a coil, a reed switch or the like can also be mounted thereon.

Further, although in the above described second embodiment an example was described in which a gold wire is used as a wire for wire bonding, the present invention is not limited thereto. For example, a wire material or a plate material including a conductive substance such as aluminum or copper or the like may also be used.

Furthermore, although in the above described third embodiment an example was described in which the spacer is constituted by a metal member, the present invention is not limited thereto, and for example, it is possible to use various kinds of materials such as a resin plate.

It should be understood that the present invention is not limited to each of the above described embodiments and the like, and naturally various changes can be made within a range that does not depart from the spirit and scope of the present invention.

What is claimed is:

1. An image pickup apparatus comprising:
 a flexible substrate defining an opening;
 a wiring pattern formed on the flexible substrate;
 an image pickup device comprising a chip,
  wherein the chip comprises:
   a front face having a light receiving area; and
   a rear face,
  wherein the chip is mounted to the flexible substrate so that the light receiving area is positioned at the opening of the flexible substrate, and
  wherein the chip is electrically connected to the wiring pattern formed on the flexible substrate;
 a rigid substrate comprising a concave surface; and
 a wiring pattern formed on the rigid substrate,
 wherein at least one section of the concave surface of the rigid substrate is set as a reference face,
 wherein at least one section of the rear face of the chip of the image pickup device is fixed to the reference face of the rigid substrate,
 wherein in a state where the at least one section of the rear face of the chip of the image pickup device is fixed to the reference face of the rigid substrate, the reference face regulates an optical axis direction of the image pickup device, and
 wherein the wiring pattern formed on the flexible substrate and the wiring pattern formed on the rigid substrate are electrically connected.

2. The image pickup apparatus according to claim 1, wherein a depth of the concave surface of the rigid substrate is set so as to be less than or equal to a thickness of the image pickup device.

3. The image pickup apparatus according to claim 1,
 wherein the image pickup device is fixed to the reference face of the concave surface via an intervening spacer member, and
 wherein a depth from an opening end of the concave surface of the rigid substrate to the reference face is set so as to be less than or equal to a sum of a thickness of the image pickup device and a thickness of the intervening spacer member.

4. The image pickup apparatus according to claim 3, wherein the intervening spacer member is a heat dissipating member.

5. The image pickup apparatus according to claim 1,
 wherein a step formed in the concave surface is set as the reference face, and wherein a step formed in a rear face side of the chip is set as a fixation face, and the fixation face is fixed to the reference face.

6. An electronic device comprising the image pickup apparatus according to claim 1.

* * * * *